United States Patent [19]

Bai et al.

[11] Patent Number: 4,486,835
[45] Date of Patent: Dec. 4, 1984

[54] APPARATUS AND TECHNIQUES FOR ELECTRIC TOMOGRAPHY

[75] Inventors: Dov Bai; Achi E. Brandt; Bruce D. Soilish, all of Rehovot, Israel

[73] Assignee: Yeda Research and Development Co. Ltd., Rehovot, Israel

[21] Appl. No.: 286,538

[22] Filed: Jul. 24, 1981

[30] Foreign Application Priority Data

May 13, 1981 [IL] Israel ........................................ 62861

[51] Int. Cl.³ .......................... G06F 15/42; A61B 5/04
[52] U.S. Cl. ..................................... 364/414; 128/734; 378/21; 378/37; 378/901; 364/415; 364/480
[58] Field of Search ................ 364/414, 415, 480–483; 250/428, 436; 378/21, 37, 901; 128/630, 734

[56] References Cited

U.S. PATENT DOCUMENTS

| | | | |
|---|---|---|---|
| 2,996,666 | 8/1961 | Baker | 364/481 |
| 3,340,867 | 9/1967 | Kubicek et al. | 128/734 |
| 4,250,894 | 2/1981 | Frei et al. | 128/630 |
| 4,263,920 | 4/1981 | Tasto et al. | 128/734 |
| 4,291,708 | 9/1981 | Frei et al. | 364/415 |

Primary Examiner—Errol A. Krass
Assistant Examiner—Kevin J. Teska
Attorney, Agent, or Firm—Browdy and Neimark

[57] ABSTRACT

Apparatus for electric tomography comprising a coupling medium for receiving an object to be examined, a plurality of electrodes disposed in the coupling medium and arranged in a three dimensional array; multiplexing apparatus for applying electric voltages at selected first pluralities of electrodes and simultaneously measuring electric currents at corresponding selected second pluralities of electrodes in a desired sequence; and computation apparatus coupled to the multiplexing apparatus for originally estimating the electrical properties at a multiplicity of locations in the object to be examined, these locations being arranged in a three dimensional imaginary grid defined in the object to be examined and subsequently correcting the conductivity estimates at each of the multiplicity of locations on the basis of the measured currents by an iterative process.

10 Claims, 16 Drawing Figures

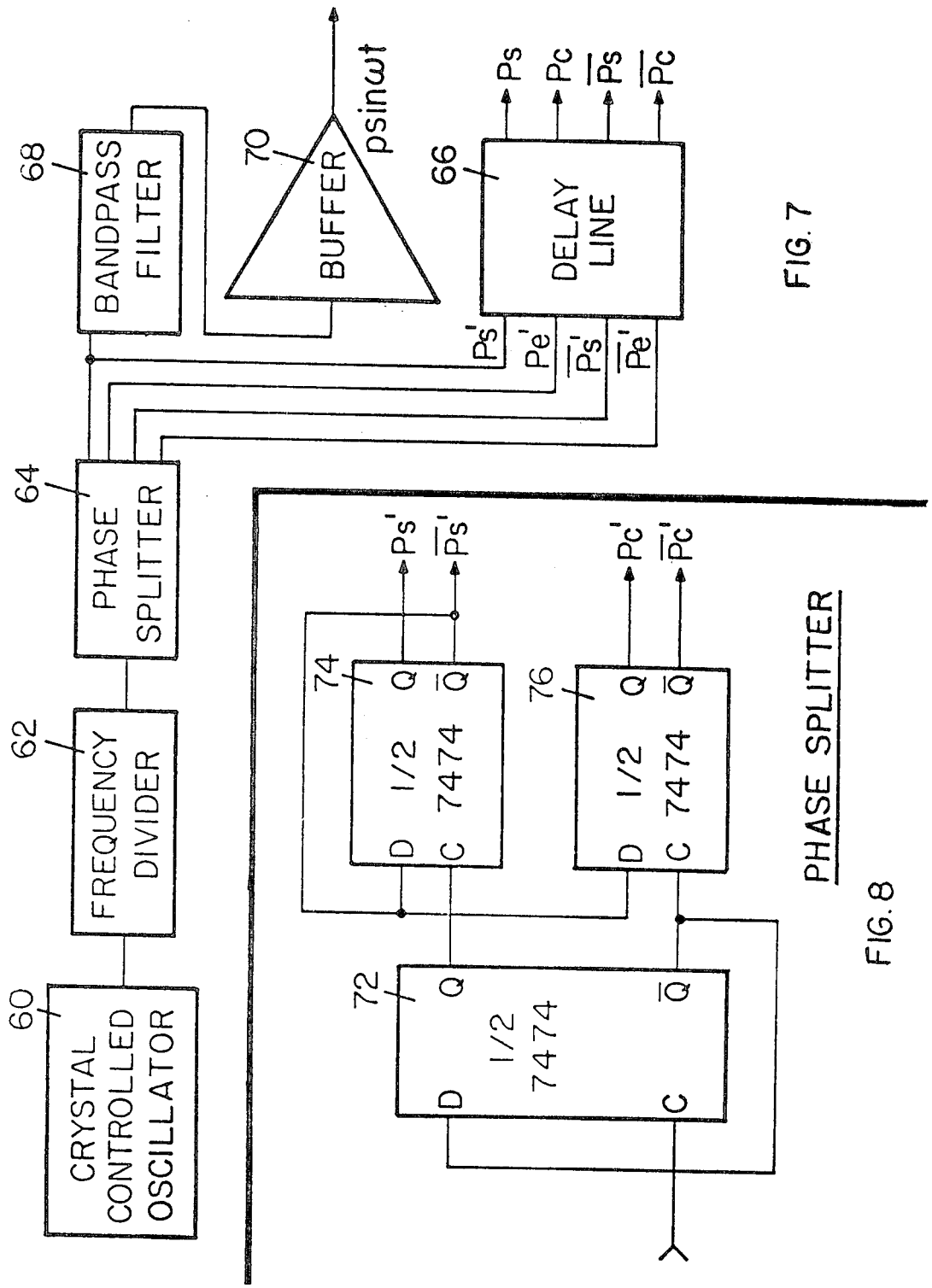

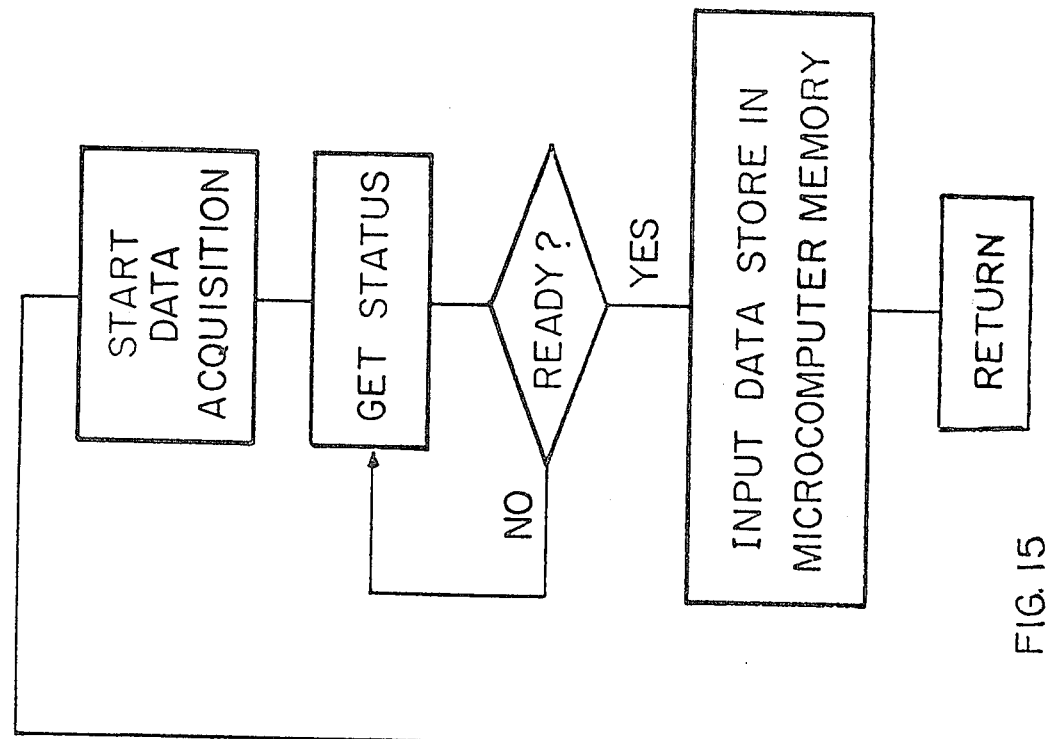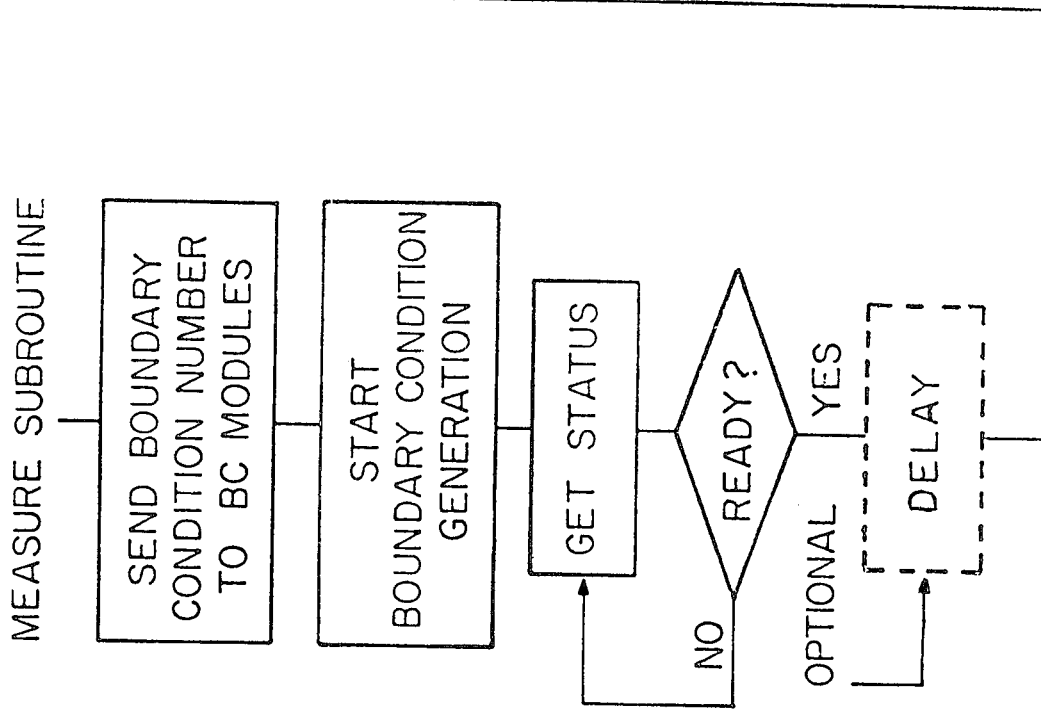
FIG. 15

APPARATUS AND TECHNIQUES FOR ELECTRIC TOMOGRAPHY

FIELD OF THE INVENTION

The present invention relates to apparatus for measuring and indicating the electrical properties of biological tissue for diagnostic purposes and to techniques for use therewith and more particularly, to apparatus and techniques for electrical tomography.

BACKGROUND OF THE INVENTION

Various objects including, for example, the interior region and organs of the human body, are known to have inhomogeneous electrical properties which may be defined in terms of conductivity and dielectric constant. Information concerning the electrical properties of human tissue may be of significant clinical value. For example, conductivity differences may indicate the presence of pulmonary edema and differences in dielectric constant may indicate the presence of breast tumors. See the following references:

1. R. P. Henderson and J. G. Webster, An impedance camera for spatially specific measurements of the thorax, IEEE Trans. Biomedical Eng., BME-35, pp 250–254, May 1978.
2. Sollish B. D., Drier Y, Hammerman E., Moshitzky M., Frei E. H. and Man B. A dielectric breast scanner, Digest of the XII International Conference on Medical and Biological Engineering and the V International Conference on Medical Physics, Jerusalem, Israel, August, 1979. Lecture 30.3.

Were it not a matter of treatment of the human body, it might be practical to measure the electrical properties of tissue by implanting a suitable electrode internally. Such a technique is clearly impractical. Therefore it is necessary to determine the electrical properties of internal tissue on the basis of electrical measurements performed on the surface of the body.

A method and a device for measuring the electrical properties of internal human tissue by means of external measurements is proposed in U.K. patent application No. 2,019,579, published on Oct. 31, 1979 and is discussed in the following references:

3. H. Schomberg, Reconstruction of spatial resistivity distribution of conducting objects from external resistance measurements, Applied Analyses and Mathematical Physics, T-41–T-42 (1979).
4. M. Tasto and H. Schomberg, Object reconstruction from projections and some non-linear extension, in Pattern Recognition and Signal Processing, edited by C. H. Chen, 1978.
5. H. Schomberg, Nonlinear image reconstruction from projections of ultrasonic travel times and electric current densities, Proc. Conf. on Mathematical Aspects of Computerized Tomography (Mathematisches Forschungsinstitut, Oberwolfach, Black Forest, F.R.G.) February 1980.

The apparatus and techniques described in the above cited U.K. patent application and in the above references employ a pair of electrode arrays disposed on opposite sides of a water tank. One of the electrodes is a continuous plate electrode, while the other is an array of a plurality of small electrodes arranged in a plane opposite the first electrode on the opposite side of the object to be examined. A current meter is connected to each of the small electrodes. A potential difference is imposed between the two opposite sides and the currents are measured.

The information obtained by measurement of the currents passing through the individual small electrodes is process in the following manner: An initial guess of the conductivity distribution of the object is made and for this purpose the resistances along straight current paths, referred to in the references as "tubes of flow" are calculated. These computed resistance values are compared with the measured values and the original estimate is corrected by backprojecting the differences along the calculated current paths, which are in fact curved, rather than straight current paths as originally postulated.

Since the number of resistances is greater than the number of measurements, the water tank is rotated around the body and data processing is done once again, using the corrected estimate as the base estimate. This process continues until a desired convergence is attained.

The technique described above is an adaptation of conventional X-ray tomographic techniques. It is believed by applicants to be an unfortunate and inappropriate adaptation for the following reasons:

The technique of "tubes of flow" is suitable for X-ray propagation since it is essentially straight-line propagation. It is not suitable for electrical currents since current does not flow in a straight line in tissue. Instead, the current flow is extremely complicated and cannot be analyzed in terms of tubes of flow or stream lines.

The failure of the proposed apparatus and technique described in the aforesaid U.K. patent application is admitted by one of the inventors therein, H. Schomberg, where he writes in reference (5) as follows: "We conclude that EC-CT as presented here is impracticable. It might be possible to enforce uniqueness by restricting the class of admissible functions or by complicating experiment and model. The first way is likely to deprive EC-CT of its potential applications. The second way will probably make the practical inverse problem unmanageable. In both cases, the difficulties caused by the insensitivity of the current density to changes in the resistivity hold on. The author therefore doubts that EC-CT based on projections of the current density will ever become a practicable, quantitative imaging method".

In summary, the major difficulty of the proposed prior art apparatus is that it employs methods of analysis useful in X-ray tomography for analysing electrical properties. The difference between X-ray tomography and current measurements is that in the X-ray technique, the straight line nature of the flow makes the analysis simpler.

An additional difficulty in the proposed prior art apparatus is that there the information is analyzed in two dimensional cross sections in order to simplify the analysis. This simplification ignores important information which is present outside of the two dimensional slice since the current flow paths are not generally planar.

As a result of the direction of the proposed prior art apparatus towards straight current flows, the available permutations of voltage distributions on the electrodes are extremely limited, thus limiting the efficiency of data collection.

SUMMARY OF THE INVENTION

The present invention seeks to provide apparatus and techniques for electric tomography which overcome the serious disadvantages associated with known proposed apparatus and techniques as described above.

There is thus provided, in accordance with an embodiment of the present invention, apparatus for electric tomography comprising: a coupling medium for receiving an object to be examined, a plurality of electrodes disposed in the coupling medium and arranged in a three dimensional array; multiplexing apparatus for applying electric voltages at selected first pluralities of electrodes and simultaneously measuring electric currents at corresponding selected second pluralities of electrodes in a desired sequence; and computation apparatus coupled to the multiplexing apparatus for originally estimating the electrical properties at a multiplicity of locations in the object to be examined, these locations being arranged in a three dimensional imaginary grid defined in the object to be examined and subsequently correcting the conductivity estimates at each of the multiplicity of locations on the basis of the measured currents by an iterative process.

Further in accordance with an embodiment of the present invention, the first pluralities of the electrodes are arranged to provide current flows through the object to be examined which are non-parallel.

It is a particular feature of the present invention that, in contrast to the proposed prior art device, the present invention takes into account to a desired level of accuracy the effect of all the object nodes on the currents measured by each electrode without requiring any a priori assumptions about current flow through calculable paths within the object.

BRIEF DESCRIPTION OF THE DRAWINGS

The present invention will be more fully understood and appreciated from the following detailed description taken in conjunction with the drawings in which:

FIG. 7 is a block diagram of the signal generator of FIG. 6;

FIG. 8 shows the phase splitter circuitry of FIG. 7;

FIGS. 14 and 15 are flow charts illustrating the operation of the computation circuitry of the present invention.

DETAILED DESCRIPTION OF THE INVENTION

The present invention will now be described in detail with reference to the drawings. By means of introduction, it should be understood that the technique of electric tomography according to the present invention includes the steps listed below and the apparatus of the present invention is operative to carry out these steps:

1. Impose a multiplicity of sequence 3-dimensional boundary conditions onto an object being studied, here in the form of voltages applied to a plurality of electrodes surrounding a body organ.
2. Measure the currents which flow through the electrodes for each of the multiplicity of boundary conditions.
3. Store the values of the measured currents in a memory.
4. Transfer the stored values of current to computation apparatus for processing.
5. Display the results, normally in the form of a reconstructed image, in gray-scale, color, or any other form.

For the sake of clarity and simplicity, the apparatus and technique of the present invention will be described with reference to exemplary measuring apparatus illustrated in FIG. 1 and defining a tank 10 having formed thereon 256 electrodes, arranged as four 8×8 arrays, disposed on the four interior sides 12, 24, 16 and 18, of the tank. It is appreciated that the number of electrodes and their density may be increased or decreased as necessary. The sixty-four electrodes in each array are arranged on the sides of the tank in a uniform manner and are typically 1 cm square and formed of stainless steel. Electrical conductors (not shown) communicate between each electrode and the outside of the tank. The tank is an insulator, and the individual electrodes are insulated from each other.

Figure 2:
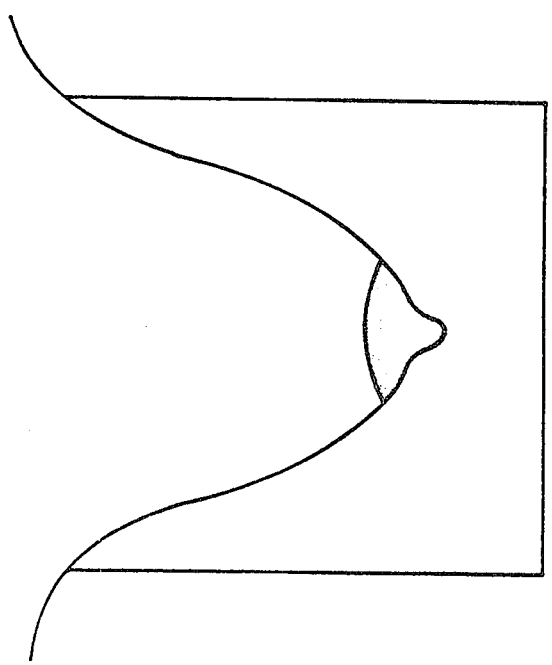
FIG. 2 shows an object to be examined disposed in the tank of FIG. 1.

FIG. 2 illustrates the disposition of a human breast in the tank and surrounded by a liquid coupling medium, such as water or any other suitable medium. The coupling medium is matched to the typical expected conductivity of the object being examined. In the case of the human tissues, the expected conductivity is approximately 1–10 millimho/cm. According to a preferred embodiment of the invention, the electrodes on each side of the tank have an unobstructed view of the breast. Typically, two such tanks are suitably placed on a support surface on which the patient lies. The following discussion concerns electric tomography of apparatus for a single tank.

The circuitry which provides a reconstruction of the electrical properties of the object being examined will now be described. For the sake of simplicity and clarity of expression the tomographic reconstruction of simple conductivity $\sigma(x)$ will be considered in a domain $\Omega$. The complex boundary voltages $p_m(x)$ and currents $i_m(x)$ are shown. These complex boundary values enable computation of complex conductivity including dielectric constant.

Figure 3:
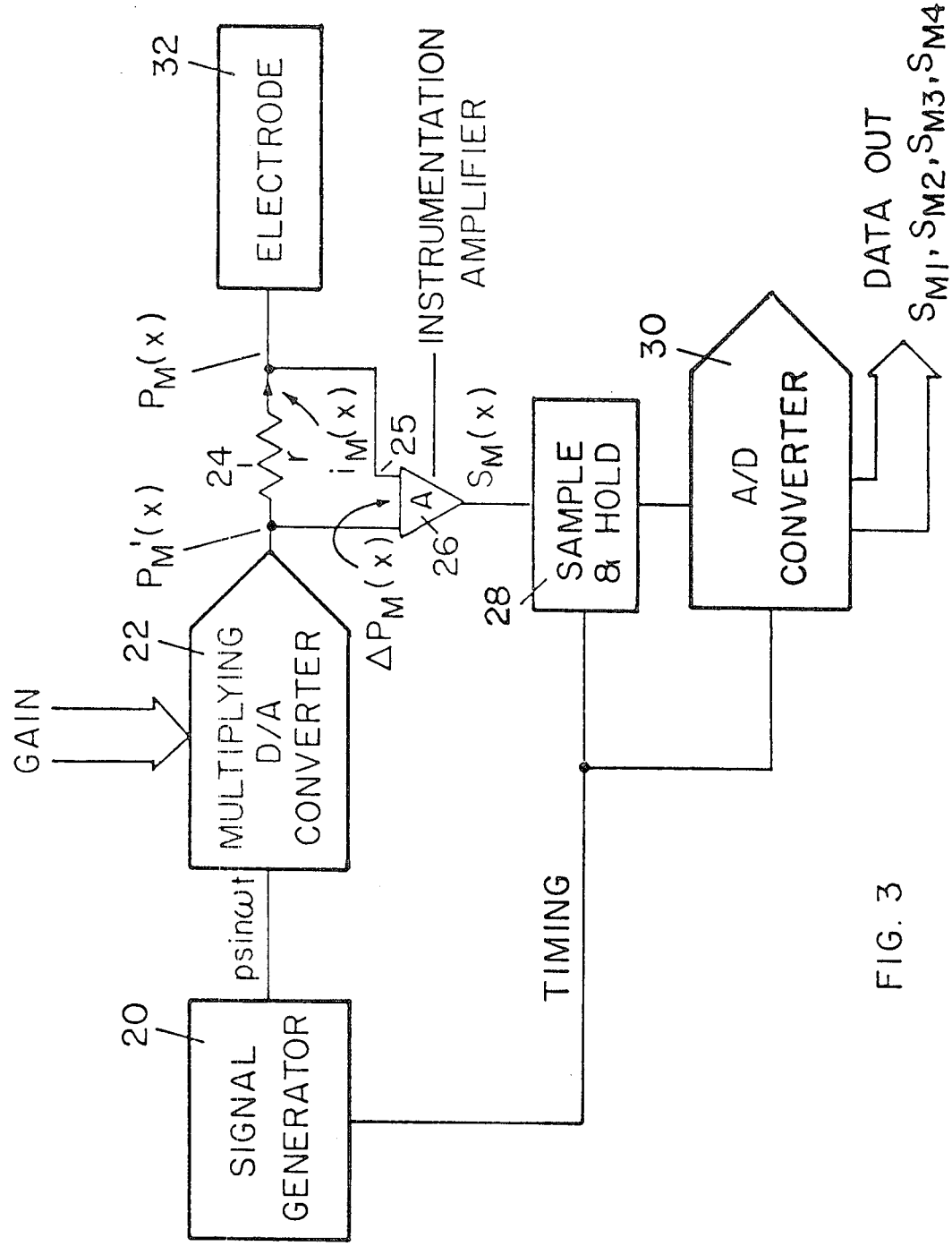
FIG. 3 shows signal processing circuitry associated with a single electrode.

Reference is now made of FIG. 3 which illustrates signal processing circuitry associated with a single electrode and comprising a signal generator 20 which provides a sinewave voltage of frequency typically between 100 Hz and 1 KHz to a multiplying D/A converter 22, such as a Datel DAC-UP8B which provides an output across a voltage dropping resistor 24. The two ends of the resistor 24 are coupled to respective inputs 25 and 27 or an instrumentation amplifier 26, which outputs to a sample and hold circuit 28.

The output of the sample and hold circuit 28 is supplied to an A/D converter 30. Timing signals from the signal generator are supplied to the sample and hold circuit 28 and to the A/D generator. The A/D converter provides the desired data output of current measurements at an electrode 32 which is coupled to input 25 of amplifier 26. Electrode 32 receives a boundary-condition establishing voltage across resistor 24. The instrumentation amplifier, sample and hold amplifier, and analog to digital converter are contained within the data acquisition submodule described later.

It may thus be appreciated that the purpose of the circuitry of FIG. 3 is two fold, i.e. to produce a specified voltage at the electrode for establishment of a boundary condition and to measure voltages which enable computation of the boundary current. These two functions are generally performed sequentially: first a boundary condition is established, then the resulting boundary current is measured.

A brief mathematical explanation of the computations involved in the solution of the boundary value problem established by the apparatus described above will now be provided.

The mathematical problem can be stated as follows:

Given a distribution of electrical properties in an object, and given an applied voltage distribution over some external boundary, it is known how to find the current flow at the boundary from a solution of the appropriate Laplace's equation. The problem is to solve the inverse Laplace's equation to reconstruct the distribution of electrical properties within the object from the known voltage distribution and current flow at the external boundary.

Generally stated, the solution to the reconstruction problem involves the following steps:
1. Positioning a three-dimensional array of electrodes surrounding the object to be examined.
2. Applying predetermined voltages to predetermined ones of the electrodes and measuring currents through certain electrodes which result from the application of the voltages.
3. Imposing for purposes of analysis an imaginary 3-dimensional grid onto the object of a desired level of resolution. Each node of the grid is allowed to assume an independent electrical parameter. The best value for the electrical parameter for each node is determined without any preconditions.
4. Carrying out an iterative process to determine the specific distribution of electrical properties at the grid nodes which provides the closest match between the measured currents at the boundary and the currents based on the specific distributions. Preferably a mean square error minimization technique is employed. Interpolation techniques may be used for providing a continuous reconstructed image.

More particularly, the reconstruction problem is solved in accordance with the following teachings:

In a dielectric medium, two properties are of interest, conductivity $\sigma$ and dielectric constant $\epsilon$. In an isotropic medium, the conductivity and dielectric constant are related to the scalar potential u by Laplace's equation:

$$\nabla \cdot [(\sigma + i\omega\epsilon)\nabla u] = 0 \quad (1)$$

where i is the imaginary operator and $\omega$ is the angular frequency.

In the more general case, one can consider complex conductivity given by the expression $$\sigma^* = \sigma + i\omega\epsilon \quad (2)$$

and complex potential given by the expression $$u^* = u + iu' \quad (3)$$

to obtain the expression:

$$\nabla \cdot [\sigma^* \nabla u^*] = 0 \quad (4)$$

However, for lower frequencies, it is convenient to consider the conductivity only. That is, if $$\omega\epsilon << \sigma \quad (5)$$

one gets $$\nabla \cdot (\sigma \nabla u) = 0 \quad (6)$$

Equation (6) is rewritten in rectilinear coordinates as follows $$\sum_{j=1}^{3} \frac{\partial}{\partial x_j}\left[ \sigma(x) \frac{\partial}{\partial x_j} u(x) \right] = o \quad x \epsilon \Omega \quad (7)$$

with boundary conditions $$u(x) = p(x) (x \epsilon \partial \Omega) \quad (8)$$

$$\sigma(x) \frac{\partial u(x)}{\partial n} = q(x) \quad (\epsilon \; x \epsilon \partial \Omega) \quad (9)$$

where $x = x_1, x_2, x_3$ is the 3-dimensional coordinate: $\Omega$ is a 3-dimensional domain, and $\partial \Omega$ is the boundary of the domain (the walls of the tank); and p(x) is the potential applied at the boundary of the domain. q(x) is the current density at boundary, $\partial/\partial n$ is the normal derivation operator. Expression (7) is solved in order to determine the potential gradient at the boundary.

The above applies to a continuous problem. In actuality, the problem is a discrete one.

Figure 1:
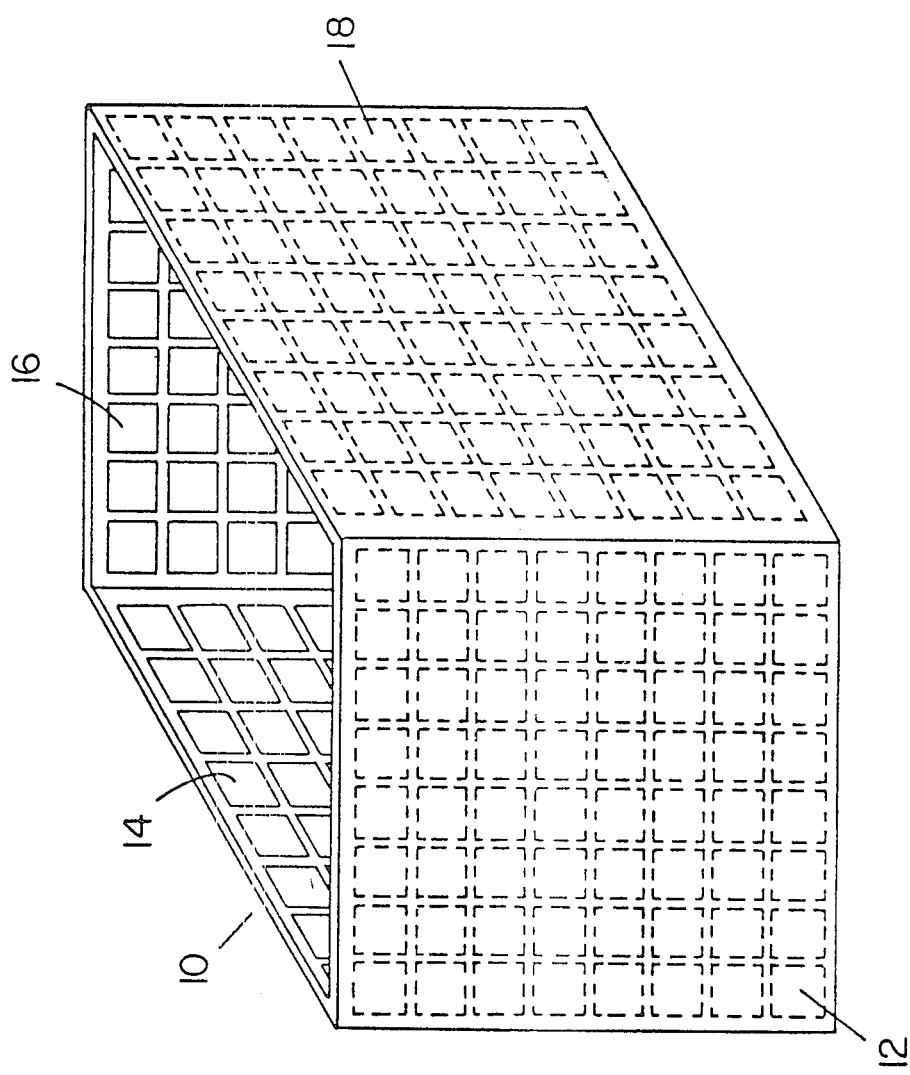
FIG. 1 is a schematic illustration of apparatus for dielectric tomography including an electrode array arranged in three dimensions in association with a tank for coupling medium.

If one considers the three dimensional arrangement of N electrodes illustrated in FIG. 1, it is appreciated that three dimensional grid is imposed, which grid defines an object space in which objects to be examined are inserted. The three dimensional grid has Q nodes and a spacing h between adjacent nodes.

At each node $q = 1, \ldots Q$ there is assigned a value of conductivity $\sigma_q$ corresponding to the conductivity of the object at the node. It may thus be understood that the electrical properties of the object are sampled at the grid nodes. The conductivities are the unknown quanities to be solved for.

A multiplicity of different boundary conditions (voltages $P_n$) are imposed on electrodes surrounding the object. A boundary condition typically comprises low-frequency sinusoidal voltages applied simultaneously to the n electrodes, in a predetermined manner. The resulting currents flowing through the n electrodes are measured. For each boundary condition a different voltage distribution is applied to the electrodes and measurement of the currents is carried out.

Denote the boundary condition index by $m, m = 1, \ldots M =, \ldots M, 1 \leq m \leq M$. where M is the total number of boundary conditions then $P_{mn}$ is the voltage applied to electrode n in boundary condition m, and $I_{mn}$ represents the current measured at electrode n in boundary condition m. The best estimate for $\sigma_q$ the conductivity at each grid node in the domain, is obtained by an interactive technique as follows:

First, a convenient initial estimate $\sigma_q^o$ is made; for example, let $\sigma_q^o$ be the conductivity of the conducting medium contained within the tank. It is appreciated that the initial estimate may be far from the true value.

The l'th iteration gets an approximation $\sigma_q^{l-1}$, $q=1$ ... Q from the previous iteration for $l=1$ (i.e. first iteration) a first convenient initial estimate is given. From this approximation, an estimate for the boundary currents, $I_{mn}^l$ is calculated by solving eq. (8), and multiplying q(x) or a mean value of it on area of the electrode by electrode area. The solution of the Laplace equations is made by using a multigrid algorithm described later. Then the difference between the actual current $I_{mn}$ and the estimated current $I_{mn}^l$ is a function of the difference between the true value of conductivity q and the estimated value of conductivity q together with an error term $E_{mn}$ as shown in the following equation:

$$\Delta I_{mn}^l = \sum_{q=1}^{Q} \alpha_{mnq}^l \Delta \sigma_q^l + E_{mn}^l \quad \begin{array}{l} m = 1, \ldots M \\ n = 1, \ldots N \end{array} \quad (10)$$

where $\Delta I_{mn}^l = I_{mn} - I_{mn}^l =$ the difference between the computed and measured currents at electrode n under boundary condition m, $\Delta \sigma_q^l = \sigma_q - \sigma_q^l =$ the difference between actual and computed conductivity at grid node q in object space and $E_{mn}^l =$ error factor including roundoff.

The array $\alpha_{mnq}^l$ is an array of linear coefficients relating the effects of changes of conductivity at each grid node to the current flow through the detector elements.

The linear coefficients are calculated as follows:

After the l'th iteration one has the set of conductivity approximations $\sigma_q^l$, and the corresponding set of currents $I_{mn}^l$. Suppose one wants to calculate $\alpha_{mnq_o}^l$. then one makes all of conductivity values at grid points other than point $q_o$ equal to $\sigma_q^\lambda$. But at grid point $q_o$ one changes the value of conductivity to $\sigma_{q_o}^l + \Delta \sigma$, Laplace's equation is now solved, and new current values at the boundaries are calculated. The differences between these new values of the currents and $I_{mn}^l$ are calculated. Then, by dividing these differences in currents by $\Delta \sigma$, one gets the set of values $\alpha_{mnq_o}^l$, n=1,... N. By repeating this process for each point $q_o$ we obtain all values of for certain intera tion l:$\alpha_{mnq}^l$, n=1, ... N; q=1, ... Q Once the array $\alpha_{mnq}^l$ has been computed, the set of equations (10) are solved to give a new estimate of $\sigma$.

Since an error term is present in each of the equations, the solution is not a simple solution of a set of linear equations. In order to obtain a good approximation for $\sigma_q^l$, it is necessary to provide a least square solution of the set of equations (10). This solution is obtained as follows:

$$E_{mn}^l = \Delta I_{mn}^l - \sum_{q=1}^{Q} \alpha_{mnq}^l \Delta \sigma_q^l \quad \begin{array}{l} m = 1, \ldots M \\ n = 1, \ldots N \end{array} \quad (11)$$

Each of the equations (11) is squared to obtain $$(E_{mn}^l)^2 = \left( \Delta I_{mn}^l - \sum_{q=1}^{Q} \alpha_{mnq}^l \Delta \sigma_q^l \right)^2 \quad \begin{array}{l} m = 1, \ldots M \\ n = 1, \ldots N \end{array} \quad (12)$$

The left hand and right hand sides of equations (12) are summed to provide:

$$\phi = \sum_{m=1}^{M} \sum_{n=1}^{N} (E_{mn}^l)^2 = \sum_{m=1}^{M} \sum_{n=1}^{N} \left( \Delta I_{mn}^l - \sum_{q=1}^{Q} \alpha_{mnq}^l \Delta \sigma_q^l \right)^2 \quad (13)$$

A solution is now sought to minimize the sum of the squares of errors. In order to obtain this solution, one differentiates the sum of the squares of errors with respect to each of the unknowns $\sigma_q$ and equates this derivative to zero. The number of equations is, of course, equal to the number of unknowns. The system of linear equations thus obtained is $$\frac{\partial \phi}{\partial \sigma_{q_o}^l} = \frac{\partial}{\partial \sigma_{q_o}^l} \left( \sum_{M=1}^{M} \sum_{n=1}^{N} (E_{mn}^l)^2 \right) = \quad (14)$$

$$\sum_{m=1}^{M} \sum_{n=1}^{N} 2 \left( \Delta I_{mn}^l - \sum_{q=1}^{Q} \alpha_{mnq}^l \Delta \sigma_q \cdot \right) \alpha_{mnq_o}^l = o$$

and may be solved by a computer using standard programs for solutions of linear equations.

Multi-grid techniques for solving equations (7) and (8) are described below:

To solve the problem numerically one proceeds as follows: The function $\sigma$ is approximated by a piecewise trilinear function $\sigma^h$ on a cubic grid with meshsize h covering the domain $\Omega$. The function $U_m$ approximated by a discrete function $U^h$ defined on the vertices $x^h$ of the grid, i.e., on points $x^h = (\nu_1 h, \nu_2 h, \nu_3 h)$ where $\nu_1$, $\nu_2$ and $\nu_3$ are integers. Equations (7) and (8) are approximated by the finite difference equations:

$$L^h U_m^h \equiv \sum_{j=1}^{3} \partial_j^h [\sigma_j^h(x^h) \partial_j^h U_m^h(x^h)] = 0, \, (x^h \epsilon G^h) \quad (15)$$

$$U_m^h(x^h) = P_m(x^h), \, (x^h \epsilon \partial G^h)$$

where $\partial_1^h \nu(x_1, x_2, x_3) = \quad (16)$ $$\frac{1}{h} \left[ \nu \left( x_1 + \frac{h}{2}, x_2, x_3 \right) - \nu \left( x_1 - \frac{h}{2}, x_2, x_3 \right) \right]$$

is the short central approximation to the derivative $\partial \nu / \partial x_1$, and $\partial_2^h$ and $\partial_3^h$ are similar approximation to $\partial / \partial x_2$ and $\partial / \partial x_3$, respectively. $G^h$ is the set of all grid points interior to $\Omega$, $\partial G^h$ is the set of grip points on $\partial \Omega$. For simplicity one assumes in this description that $\partial \Omega$ coincides with pieces of grid planes. This assumption can easily be eliminated by standard techniques.

The above discretization is second-order. That is, the error is $O(h^2)$.

This is how we described a multigrid method for fast solution of the direct equations (15)–(16) for one fixed m. One therefore omits the subscript m. At various instances of the solution process, one has on $G^h$ an approximation to $U^h$, which is generally denoted by $u^h$.

To obtain a fast solution to (7) via the multi-grid method, one adds to $G^h$ a sequence of coarser uniform grids. Let $G^H$ be such a coarser grid; e.g., let the grid-lines of $G^H$ by every other grid-line of $G^h$, so that its mesh-size is H=2h, and its points are $x^H=(v_1H, v_2H, v_3H)$ where $v_1$ are integers.

Since on coarser grids one has equations similar to (15)–(16) but with non-vanishing right-hand sides, one generalizes the equations on th finest grid also, and describes the solution to the inhomogeneous equation $$L^hU^h(x^h)=F^h(x^h),(x^h\epsilon G^h)$$

$$U^h(x^h)=p(x^h),(x^h\epsilon\partial G^h) \quad (18)$$

One way of inexpensively obtaining an approximate solution $u^h$ to (7) is to first obtain an (approximate) solution $u^H$ to the corresponding coarser problem $$L^HU^H(x^H)=F^H(x^H),(x^H\epsilon G^H)$$

$$U^H(x^H)=p(x^H),(x^H\epsilon\partial G^H) \quad (19)$$

(which is much less expensive to solve since it contains far fewer unknowns) and then to interpolate $u^H$ to the fine grid:

$$u^h=I_H^h u^H. \quad (20)$$

The symbol $I_H^h$ stands for the Operation of inerpolating from $G^H$ to $G^h$.

How good the approximation (20) is depends on the smoothness of the solution $U^h$. In some cases $U^h$ is so smooth that, if the interpolation $I_H^h$ and the coarse grip operator $L^H$ are of order high enough to exploit that smoothness, than $u^h$ obtained by (20) satisfies $$||u^h-U^h||\leq||U-U^h||, \quad (21)$$

in some suitable norm. This means that $u^h$ solves (19) "to the level of the truncation error", which is all we can meaningfully require. In such cases, however, the fine grid $G^h$ is not really needed: the coarser grid $G^H$ already yields a solution with the required accuracy. If $G^h$ is at all needed, the first approximation (20) will require a considerable improvement.

Can one compute a correction to $u^h$ again by some interpolation from the coarse grid $G^H$? Namely, can one somehow approximate the error $V^h=U^h-u^h$ by some $V^H$ computed on $G^H$? Normally, the answer is no. If $u^H$ in (20) is a good enough approximation to $U^H$, then $V^h$ will be a rapidly oscillating function that is not visible on the coarse grid $G^H$. Therefore, before one can reuse the coarse grids, the effor $V^h$ should be smoothed out.

An efficient smoothing is obtained by relaxation sweeps. A standard example is the Gauss-Seidel relaxation sweep. This is a process in which all points $x^h$ of $G^h$ are scanned one by one in some prescribed order. At each point the old value $u^h(x^h)$ is replaced by a new value, which is computed so that (18) is satisfied at that particular point $x^h$. Such a sweep having been completed, the system (18) is not yet solved, because its equations are coupled to each other; but the new approxmation $u^h$ is hopefully "better" than the old one.

In fact, a well-known and extensively used method for solving (18) is by a long sequence of relaxation sweeps. The trouble is the slowness with which such a sequence converges. The larger the grid, the slower the convergence. The reason is the local nature of the relaxation process. It solves the equations locally, with only slight global effect. In other words, relaxation can have only a small impact (per sweep) on smooth errors, since each errors exhibit only small local errors (small residuals) compared with their own magnitude. On the other hand, relaxation sweeps can be very efficient in performing the local task of smoothing the error. In just a few sweeps of a suitable relaxation scheme, the high-frequency components of the error (i.e. components with wavelength comparable to h) are reduced by an order of magnitude.

Thus, after a few relaxation sweeps, the error $V^h$ is smooth. Hence a good approximation of $V^H$ to it can inexpensively be computed on the coarser grid $G^H$. For this purpose, the fine-grid is provided:

$$L^hV^h(x^h)=r^h(x^h),(x^h\epsilon G^h)$$

$$V^h(x^h)=0,(x^h\epsilon\partial G^h) \quad (22)$$

where, $$r^h=F^h-L^hu^h, \quad (23)$$

is approximated by the coarse-grid equation $$(L^HV^H)(X^H)=(I_h^Hr^h)(x^h),(X^H\epsilon G^H)$$

$$V^H(X^H)=0,(X^H\epsilon\partial G^H) \quad (24)$$

where $I_h^H$ is an interpolation operator (weighted averging) from $G^h$ to $G^H$.

Once (24) is approximately solved (in a way to be discussed below), its approximate solution $v^H$ is interpolated to the fine grid and used to correct the old approximation there:

$$u_{NEW}^h=u_{OLD}^h+I_H^hv^H. \quad (25)$$

In summary: To solve the fine-grid equations (18), an initial approximation (20) is obtained from an approximate solution $u^H$ to the coarse grid equation (19). Then the approximation is improved by a "multi-grid cycle". This cycle includes a couple of relaxation sweeps followed by the "coarse-grid correction" (25), in which $v^H$ is an approximate solution to the coarse-grid correction equations (24).

At the end of the multi-grid cycle the approximation $u^h$ will satisfy (21) and therefore require no further improvement.

If for any reason a greater accuracy in solving (7) is desired, additional multi-grid cycles can be performed. Each cycle which includes three sweeps of Gauss-Seidel relaxation will reduce $||u^h-U^h||$ by a factor of about 0.08.

One must still specify how the coarse-grid equations, first (19) and later (24), are actually solved. They are solved in the same way that (18) is solved, namely, by a combination of relaxation sweeps and coarse-grid corrections, using a grid still coarser than $G^H$.

Figure 4:
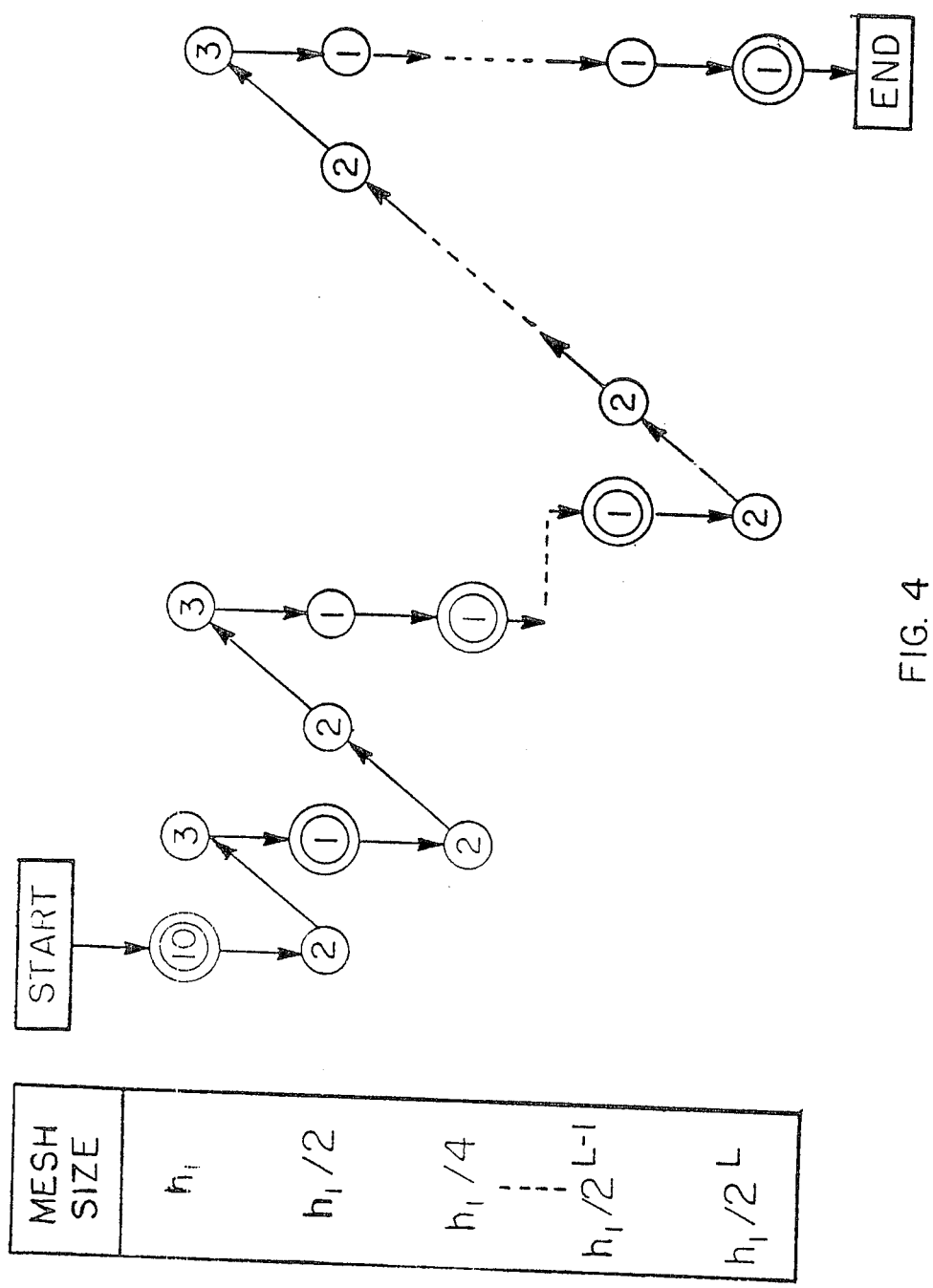
FIG. 4 is a flow chart illustrating mathematical computations used in the invention.

The full algorithm has several variations. One is illustrated in FIG. 4. In this description $V^H$ and $v^h$ is freely replaced by $U^H$ and $u^h$, respectively, at the stage of solving the $G^H$ equations (20). Shown in each circle is the number of relaxation sweeps (on the grid corresponding to that line) performed at each stage. A double circle indicates the stage where the error on that level is guaranteed to be less than the truncation error. The transfer ↓ is the first-approximation interpolation (20). The transfer ↗ back to the coarse grid introduces there equation (24) as well as the first approximation $\mu^H=0$. Where the modified arrow ↗ is shown, equation (9) can be modified to include-extrapolation (see Section 10). The transfer ↓ is the correction interpolation (14).

In case the conductivity function $\sigma$ is strongly discontinuous (i.e., changing by orders of magnitude from one region to another), special care should be exercised in choosing the interpolation operators $I_H{}^h$ and $I_h{}^H$ and the coarse-grid operator $L^H$. But for the problems at hand $\sigma$ is not expected to behave that badly, and simple linear interpolations can be used.

From FIG. 4 it can be shown that the number of computer operations (most of them additons) used by the algorithm in solving the three-dimensional problem (15)–(16) is about 23n, where n is the number of points in $G^h$. If P parallel processors are available, they can fully be exploited by the algorithm (by making the relaxation in red-black ordering; so that about 23n/P computer steps would be used in the direct solution of (15)–(16) (assuming $P < n/(\log_2 n)^2$). The storage requirement is minimal. Only 4/3n single-precision words are used by the above algorithm. Certain other versions can operate with a storage which is much smaller than n without using any external memory.

Returning now to a consideration of the circuitry of FIG. 3, it is noted in the foregoing mathematical description that a potential $p_m(x)$ is placed on elements (i.e. electrodes) ×on the boundary of domain $\Omega$, where m represents one of M boundary conditions. The generated potential $p_m'(x)$ is obtained by multiplying the input sinewave by the gain represented by the multiplying input to the D-A converter 22.

Resistor 24 which is placed in series between the D-A converter 22 and the corresponding electrode 32 causes the net voltage at the electrode 32 to be $$P_m(x) = P_m'(x) - \Delta P_m(x) \quad (26)$$

where $$\Delta P_m(x) = r i_m(x) \quad (27)$$

In general $$\Delta P_m(x)/P_m(x) << 1 \quad (28)$$

and therefore $$P_m(x) \sim P_m'(x) \quad (29)$$

For example, a typical value of $p_m(x)$ is approximately 1 Volt and $i_m(x)$ is less than 100 microamperes. Thus resistor 24 with a value of typically 100 ohms causes a voltage drop of a maximum of 10 millivolts. In any event, the applied voltage $p_m(x)$ can be calculated from the generated voltage $p_m'(x)$ and the measured voltage drop $\Delta p_m(x)$.

Once the voltage drops $\Delta p_m(x)$ is known, the current $i_m(x)$ is determined as follows: The voltage drop is multiplied by amplifier 26 having a gain A, typically 1000, which for the typical values for the voltages, currents and resistances mentioned above, yields a maximum output signal of 10 volts. The amplified voltage drop $A\Delta p_m(x)$ is then digitized by the combination of smple and hold circuit 28 and the A-D converter 30.

In the general case, the current $i_m(x)$ is complex and can be described as follows:

$$i_m(x) = i_{ms}(x) \sin \omega t + i_{mc} \cos \omega t \quad (30)$$

where $i_{ms}$ and $i_{mc}$ represent the in-phase and quadrant components, respectively, of the current $i_m$ with respect to the applied voltage $p_m'$.

The two components of the current are obtained by a four-phase technique which is described in U.S. Pat. No. 4,291,708 of the present assignee. Briefly described, the technique involves sampling the amplified voltage drop $A\Delta p_m(x)$ and digitizing the samples at four phases of the input sinewave $p_m'(x)$ for which the phase angle $\phi = \omega t$ is 0, $\pi/2$, $\pi$ and $3\pi/2$ respectively.

From equations (27) and (30) one determines the voltage at the sample and hold circuit 28 to be:

$$S_m(x) = A\Delta P_m(x) = A r[i_{ms}(x) \sin \omega t + i_{mc} \cos \omega t] \quad (31)$$

If one denotes the voltage drops at the four phases as $p_{m1}(x)$–$p_{m4}(x)$, one obtains the following expressions for the sampled and digitized voltages at the four phases. A DC offset $P_{os}$ is included to represent the offset introduced by the instrumentation amplifier 26 and the sample and hold 28. The voltages set forth below are stored in a digital memory.

$$S_{m1}(x) = A r i_{mc}(x) + P_{os}$$

$$S_{m2}(x) = A r i_{mc}(x) + P_{os}$$

$$S_{m3}(x) = A r i_{mc}(x) + P_{os}$$

$$S_{m4}(x) = A r i_{mc}(x) + P_{os} \quad (32)$$

The current $i_m(x)$ is then computed from the measured voltages $s_{m1}(x) \ldots s_{m4}(x)$ from expressions (32) and appear as follows:

$$i_{ms}(x) = \frac{S_{m2}(x) - S_{m4}(x)}{2Ar} \quad (33)$$

$$i_{mc}(x) = \frac{S_{m1}(x) - S_{m3}(x)}{sAr}$$

The DC offset $P_{os}$ cancels out provided that it remains constant over a single cycle of the applied voltage $p_m'(x)$.

The average boundary current density for the electrode can be approximated from the measured boundary current by the equation:

$$q_m(x) = i_m(x)/S \quad (34)$$

where S is the electrode surface area.

It is appreciated that in the present embodiment, computations according to equations (33) and (34) are carried out off line and that the measurement technique provided by the circuitry of FIG. 3 relates exclusively to the production of voltage $p_m'$ and the measurement of voltages $s_{m1}, \ldots s_{m4}$. The boundary voltage $p_m$ and the boundary current density $q_m$ are calculated from $p_m'$ and $s_{m1}, \ldots s_{m4}$ using equations (26), (33) and (34).

Figure 5:
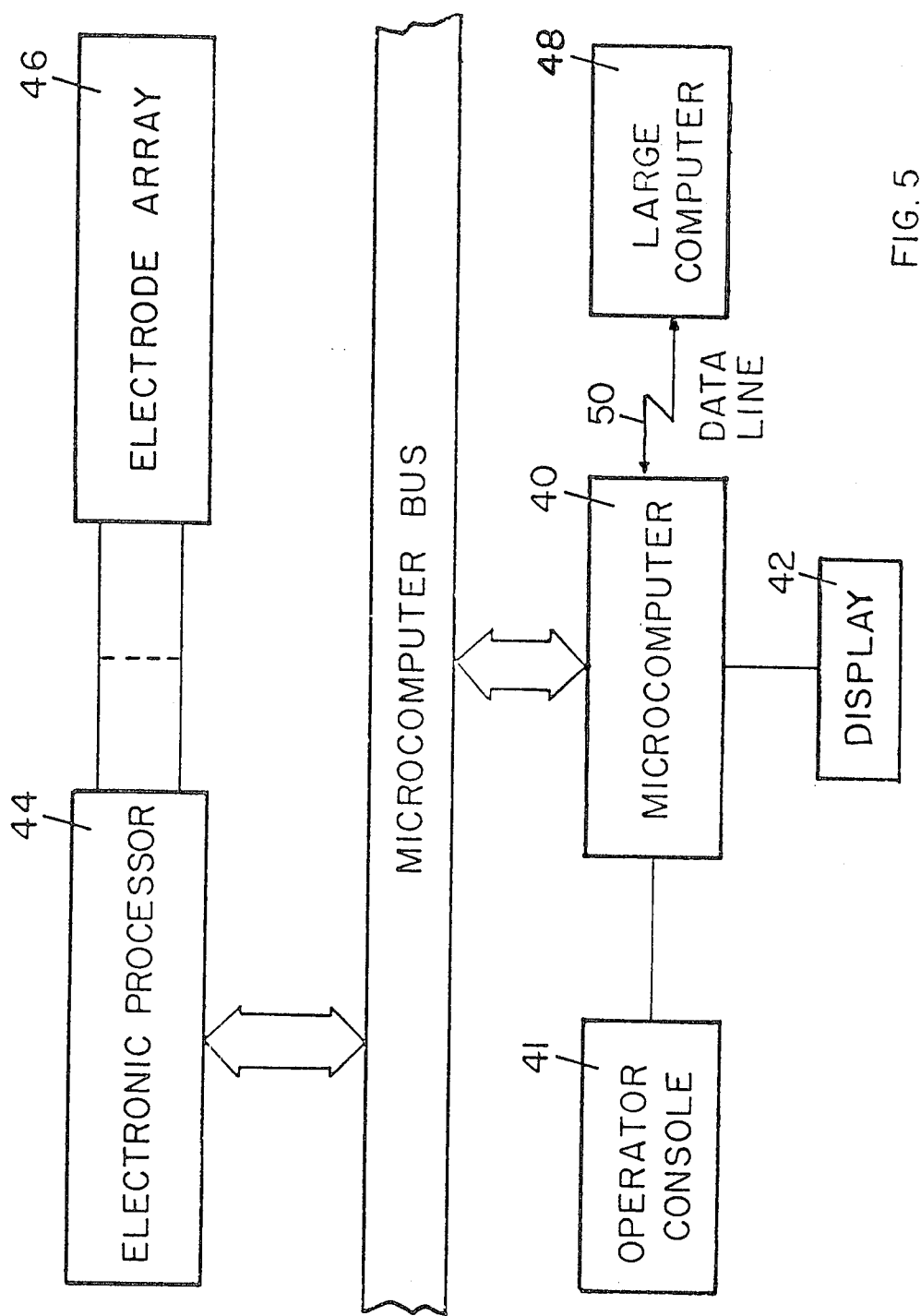
FIG. 5 is a general block diagram of the computation circuitry of the invention.

Reference is now made to FIG. 5 which illustrates in block diagram form apparatus for electric tomography constructed and operative in accordance with an embodiment of the present invention, and comprising a microcomputer 40 with associated operator console and display 42 such as a Processor Technology SOL 20 based on the Intel 8080A microprocessor and a Sanyo VM 4209 TV monitor. The microcomputer system may also comprise a 48K static memory and a floppy disk system and typically uses a S-100 bus to communicate with an electronic processor 44 which in turn communicates with the electrode array 46, of the type described in exemplary form above. The microcomputer 40 communicates via a data line with a large computer 48 via a data link 50 such as an RS 232 serial ASCII data interface. A suitable large computer is an IBM 370/165 with serial ASCII data link.

Figure 6:
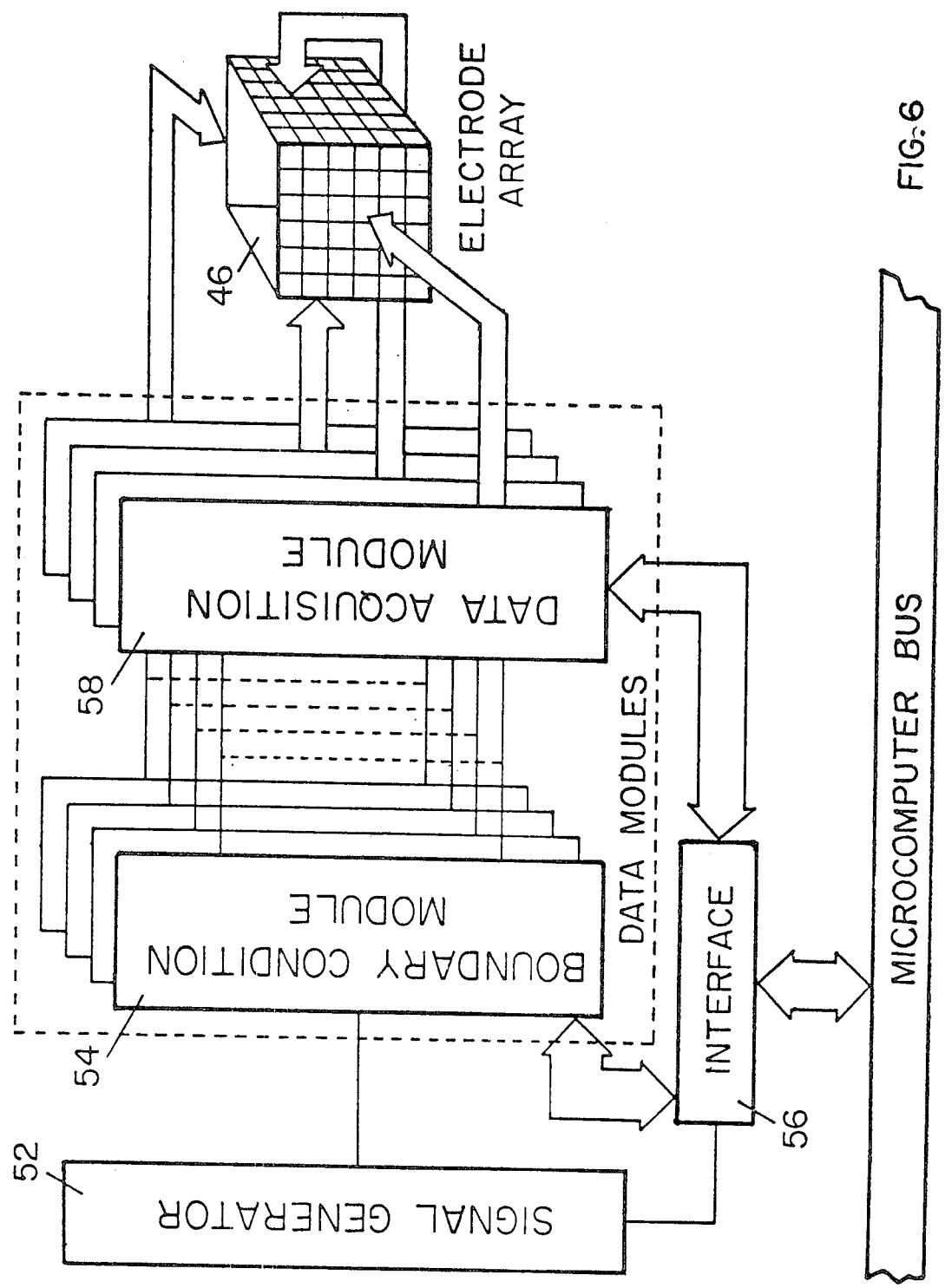
FIG. 6 is a block diagram of a portion of the circuitry of FIG. 5.

Reference is now made to FIG. 6 which illustrates the major elements of the electronic process 44 of FIG. 5. The electronic processor comprises a signal generator 52 which provides a signal output to a boundary condition module 54 and to an interface circuit 56. The boundary condition module 54 communicates with a data acquisition module 58, which in turn is connected to the electrode array 46. The processor 44 comprises four modules 54 and four modules 58 which are organized into four data modules each comprising a boundary condition module 54 and data acquisition module 58. Each data module operates with 64 electrodes and is operative to generate the boundary conditions and measure the resultant voltage drops across small sensing resistors in the manner described above in connection with FIG. 3. In the illustrated embodiment, each data module communicates with 64 electrodes along one wall of the tank of FIG. 1.

The boundary condition and data acquisition modules are identical with the following exceptions:
1. Each boundary condition module contains its own boundary conditions stored in a Read-Only-Memory.
2. Each data acquisition module contains its own data storage memory. The memory locations are contiguously addressed from one module to the next.

The commands to all data modules are transferred simultaneously by the interface, acting in response to commands issued by the microcomputer 40 (FIG. 5) over its bus and are acquired simultaneously by all of the data modules. The data is transferred sequentially from the data modules to the microcomputer via the interface and bus.

Reference is now made to FIG. 7 which illustrates the signal generator 52 of the apparatus of FIG. 6. The signal generator comprises a crystal-controlled oscillator 60, which outputs to a frequency divider 62 which in turn outputs to a phase splitter 64. The phase splitter 64 provides four outputs to a delay line 66 and provides one output to a bandpass filter 68, which outputs via a buffer amplifier 70.

As seen in FIG. 8, the phase splitter 64 comprises three halves of 7474 flip flop chips arranged as illustrated to receive an input at a C input of a first flip flop 72 and to provide respective Q and $\bar{Q}$ outputs to the respective C inputs of flip flops 74 and 76. The D and $\bar{Q}$ terminals of flip flops 74 and 76 are interconnected as is the D terminal of flip flop 74 and the D terminal of flip flop 76.

The operation of the signal generator 52 of FIG. 7 will now be described briefly. Assuming that a final frequency output of 2 kHz is required, a crystal controlled oscillator 60 having a frequency of 4 MHz is then used. The frequency divider 62 divides this frequency by 500 to provide an 8 KHz square wave. Phase splitter 64 divides the signal by four, producing a pair of square waves of frequency 2 kHz displaced in time from each other by one-quarter cycle.

One of the outputs of the phase splitter 64, identified as $p_s$, is filtered by the high Q bandpass filter 68 and buffered by amplifier 70 to provide a sinewave signal p sin 2 ft where f is the frequency of the square waves. The in-phase squarewave $p_s$, the quadrature squarewave $p_c$, and their conjugates $\bar{p}_s$ and $\bar{p}_c$ are delayed by the digital delay line 66 to compensate for the delay introduced by the bandpass filter and buffer amplifier 68 and 70 respectively. The delay is adjusted so that $p_s$ goes high when $\omega t=0, 2\pi, 4\pi, \ldots$. Then the four phases of the sinewave required for equation 33 occur at the positive transitions of $p_s, p_c, \bar{p}_s, \bar{p}_c$. These four digital timing signals are provided to interface 56 (FIG. 6).

Figure 9:
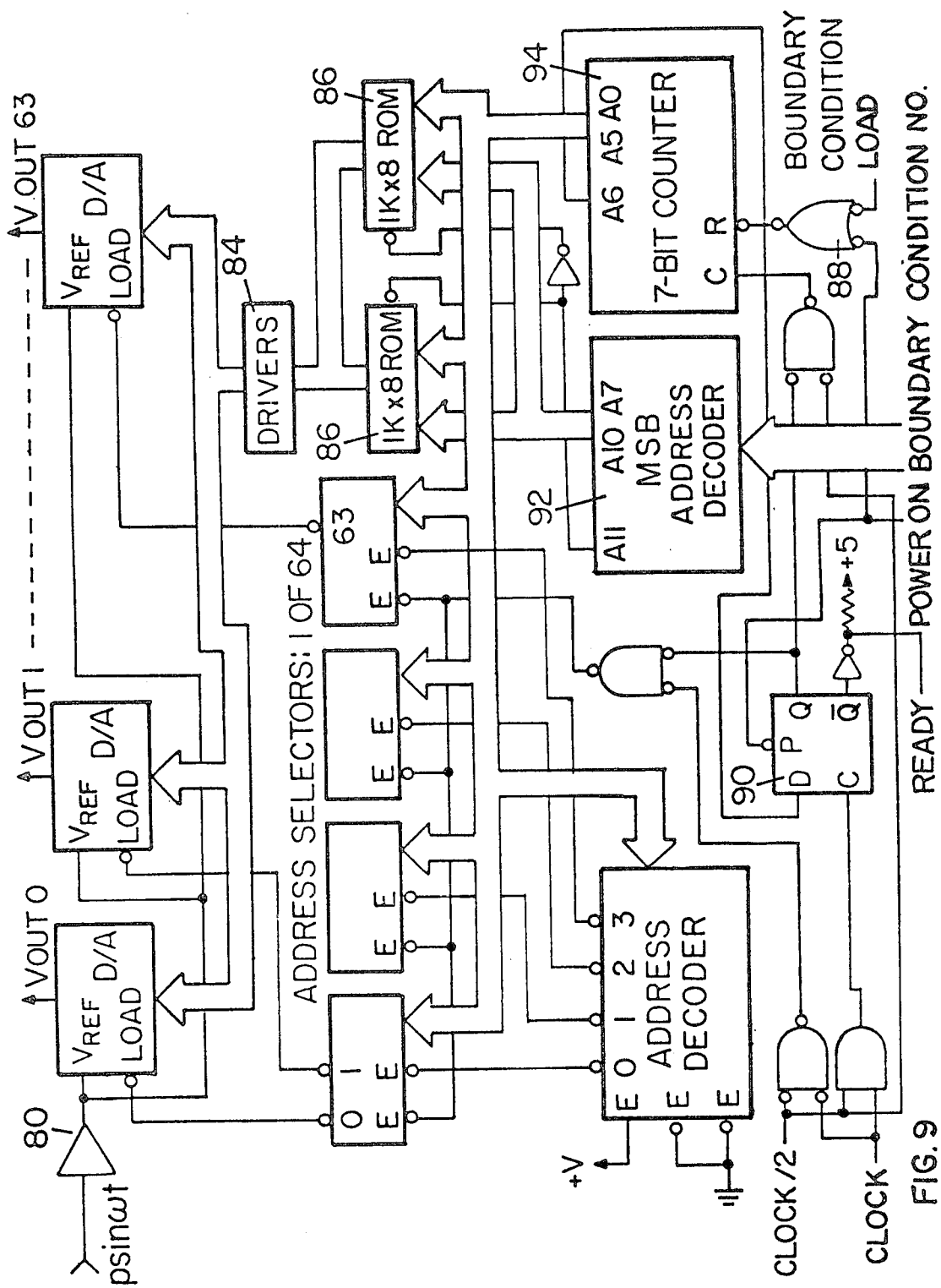
FIG. 9–12 are block diagram illustrations of portions of the circuitry of FIG. 6.

Reference is now made to FIG. 9 which illustrates a boundary condition module 54 (FIG. 6). As noted above, each module controls one side of the tank of FIG. 1. The module comprises a buffer amplifier 80 which receives the sinewave output fromn the signal generator 52 and which provides an output to 64 D/A converters corresponding to the 64 electrodes controlled by the module. The D/A converters, indicated by reference numeral 82 typically comprise latched 8 bit multiplying digital to analog converters, which receive a gain input via drivers 84 from a 2K byte Read-Only-Memory 86. ROM 86 is partitioned into 32 blocks of 64 bytes each, corresponding to 32 alternative sets of boundary conditions.

Control circuitry 88 conprising an arrangement of a flip flop 90 and a plurality of gates as illustrated, provides a 5 bit address corresponding to the beginning of one of the 32 memory blocks, depending on the boundary condition. This address is supplied to an MSB Address Decoder 92.

A seven bit counter 94 is operative upon receipt of a START command to begin counting, thereby sequentially addressing each D/A converter. For a given converter x and boundary condition m, an 8 bit word $k_m(x)$, read from the ROM memory 86 is latched into the built in register of the D/A converter. Thus after 64 counts, a pattern of 64 8-bit words has been latched into the D/A converters 82. The output of each D/A converter is an analog voltage $p_m(x)=k_m(x)p \sin \omega t$. It may thus be appreciated that the set of 64 analog voltages represents one boundary condition.

The 64 voltage outputs pass through the data acquisition module and then on to a block of 64 electrodes.

When line A6 of counter 94 gives high upon completion of the 64 bit count cycle, the boundary condition module produces a READY signal which is transferred to the microcomputer via the controller. The boundary voltage pattern remains until a new boundary condition is specified. All of the modules receive a simultaneous START command.

It is appreciated that the data contained in the ROMs of the individual modules is not normally the same since each given boundary conditions may call for different configurations of electrodes to be energized at different walls of the tank. For example, one boundary condition may require all 64 elements of one side of the tank to be at a potential V and all 64 electrodes at the opposite side of the tank to be at ground potential and the other two sides of the tank to display a linearly-decreasing potential from V along one edge to zero at the other. Whatever the conditions, the boundary values for each planar array of electrodes forming a side of the tank are generated in parallel by the four modules.

Figure 10:
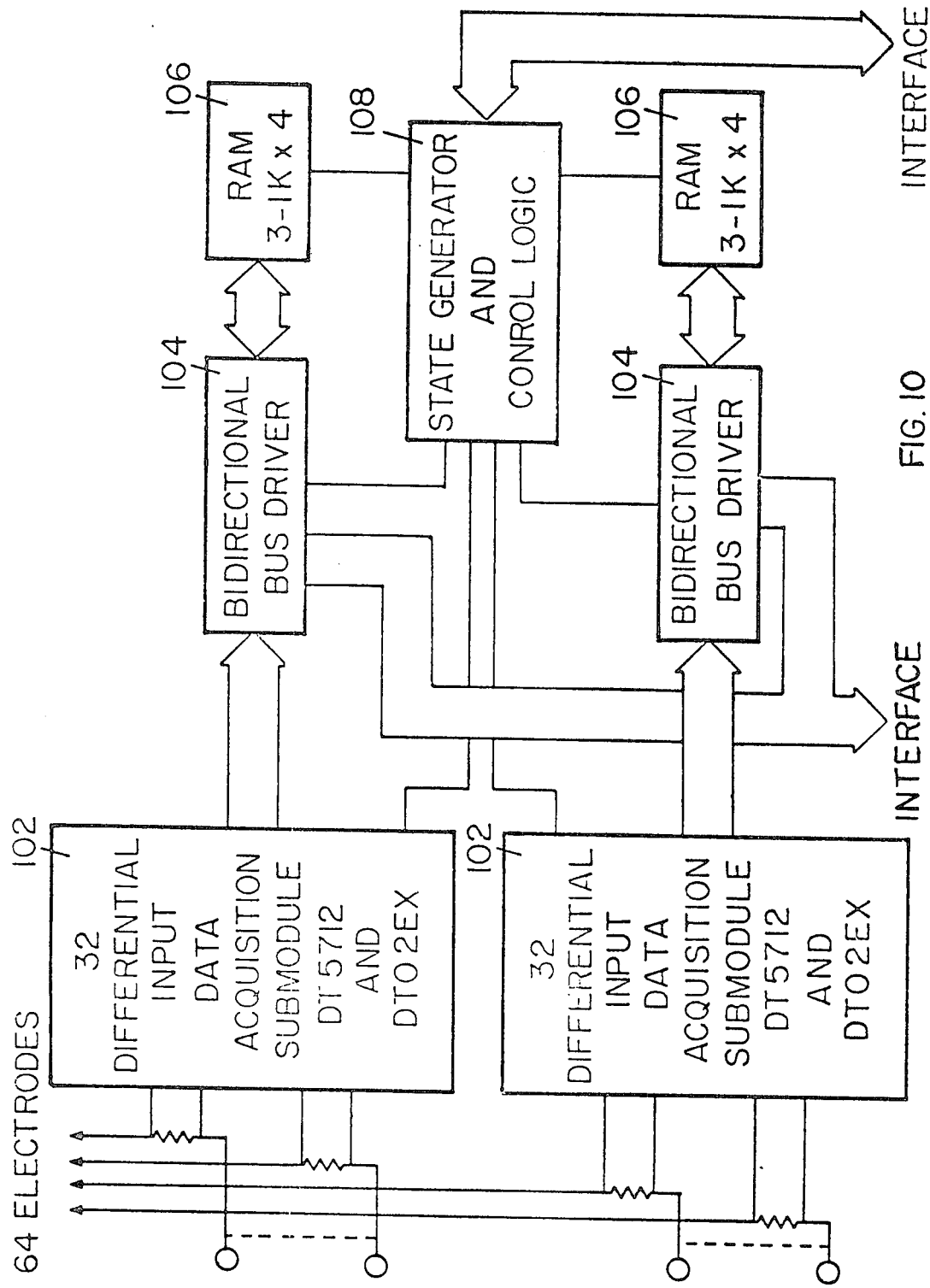
Figure 11:
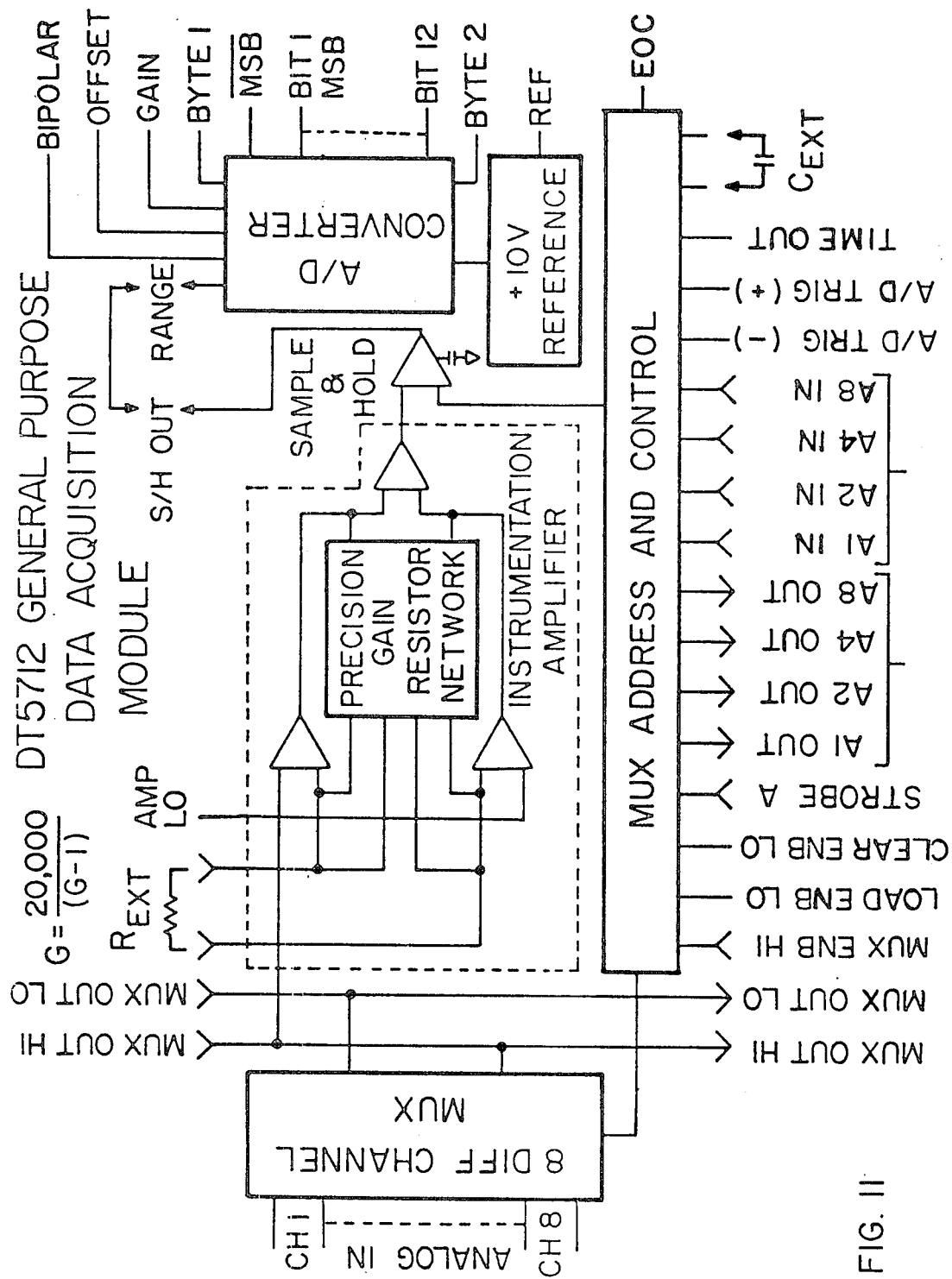
Figures 1, 11:
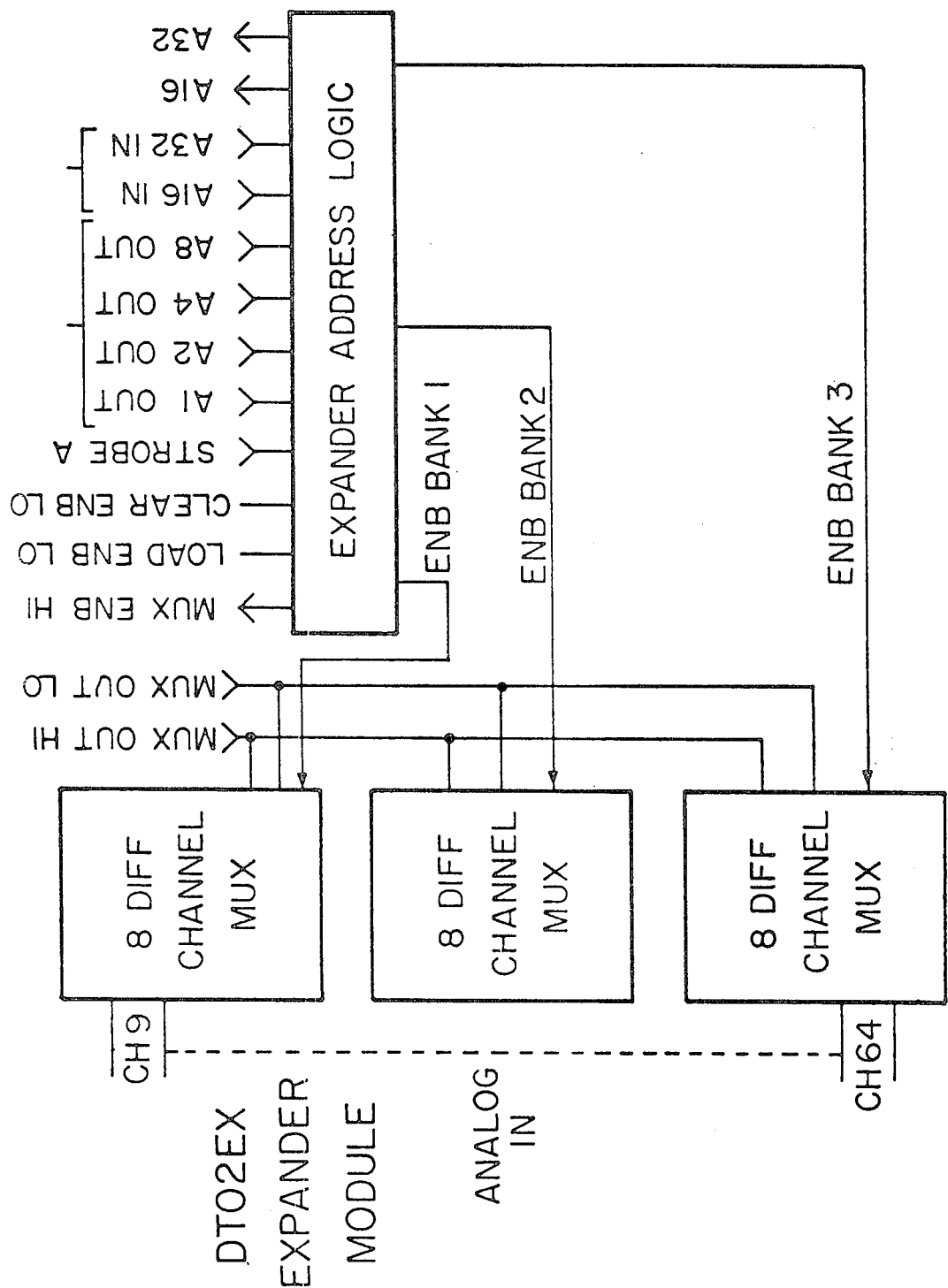
Figure 12:
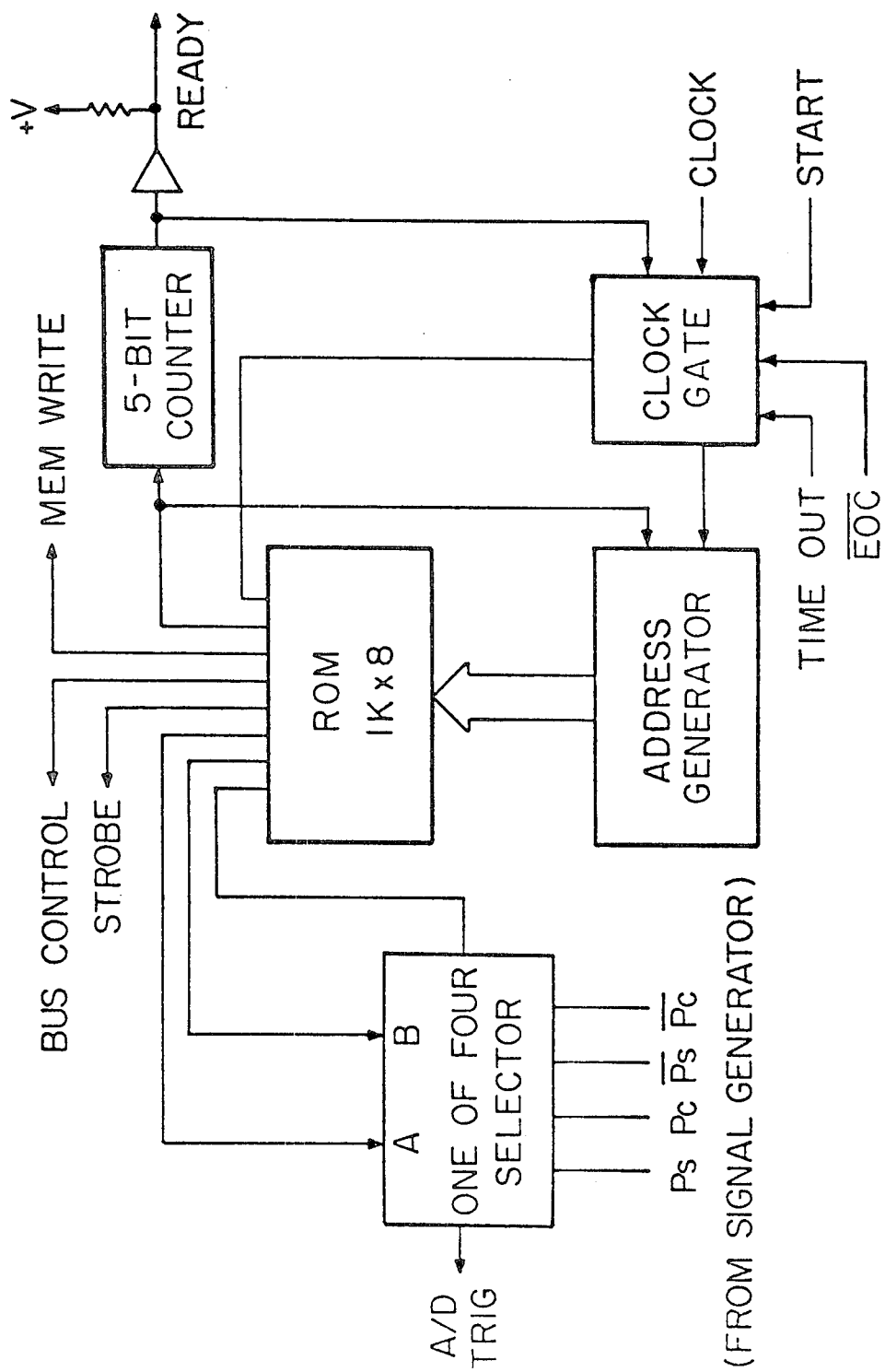

Reference is now made to FIGS. 10-12 which illustrate the data acquisition module 58 of FIG. 6. As is the case for the boundary condition module, each module in the illustrated embodiment is capable of handling 64 electrodes which are all arranged along a wall of the tank.

As seen in FIG. 10, the data acqusition module comprises an array of 64 voltage dropping resistors 100 which are couples to inputs of two 32 differential input data acquisition submodules 102 DT 5712 and DT02EX manufactured by Data Translation Corporation which are connected to the diagram of FIG. 11.

The outputs of the submodules 102 are supplied to bidirectional bus drivers 104 which communicate with interface 56 and with respective RAMs 106, each of which comprises $3\perp K \times 4$ bytes. A ROM based state address generator and control circuit 108 operates the RAMS and the submodules 102, and is controlled through interface 56.

The operation of the data acqusition module will now be summarized:

Upon receipt of a START command via interface 56, the state address generator 108 is reset and begins advancing. Each address of the ROM generates a single state comprising 8 control signals. The control signals select an input of the submodules 102, generate the 4-phase timing for sampling and measuring the data and store the results in the RAMs 106. The operation of the state generator 108 is halted during time-out periods such as multiplex-busy and A/D busy. Upon completion of a state sequence for a single electrode, a 6-bit counter advances by a single count. When the MSB of the counter gives high, a READY signal is generated to notify the microcomputer (FIG. 5) that all the data has been acquired.

The RAM addresses are arranged contiguously from one module to the next and the data is stored simultaneously in all modules. When the microcomputer transfers the data from the RAMs 106 to its own memory, the RAMs are addressed sequentially.

Each RAM 106 is formed of a set of 3-2114 RAMS and is capable of storing data from up to 8 cycles per electrode. The total maximum data stored for the four modules is 8K-12 but words, This data is read into the microcomputer memory as 12K-8 bit words for each boundary condition.

Figure 13:
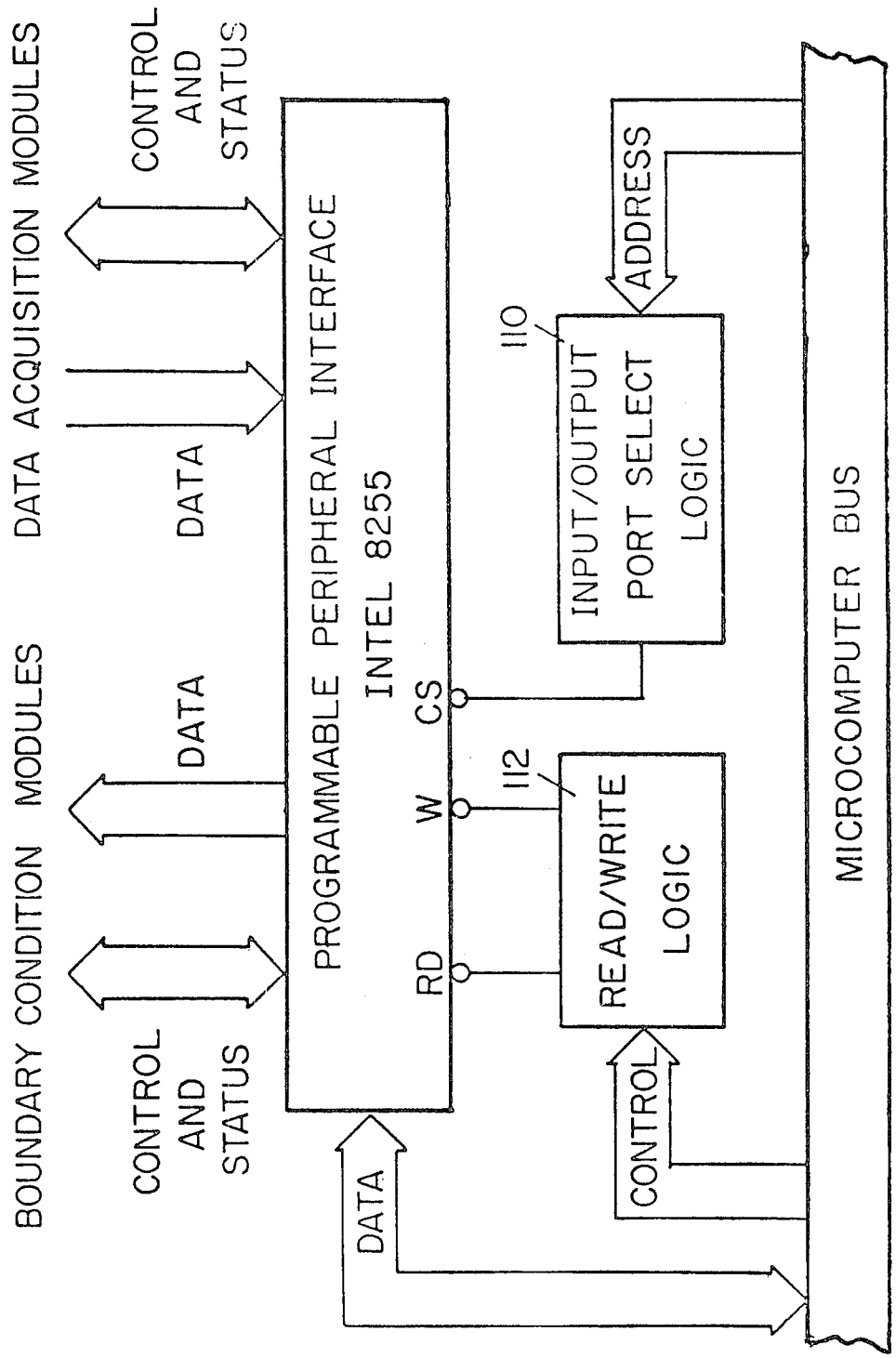
FIG. 13 is a block diagram illustration of a portion of the circuitry of FIG. 5.

Reference is now made to FIG. 13 which illustrates the interface 56 shown in FIG. 6. The interface is based on an Intel 8255 programmable peripheral interface and includes port select logic 110 which generates a chip-select signal upon sensing the address corresponding to the required port. Read-write logic 112 determines whether the selected port is input or output. Data is transferred over an 8-bit directional bus.

Figure 14:
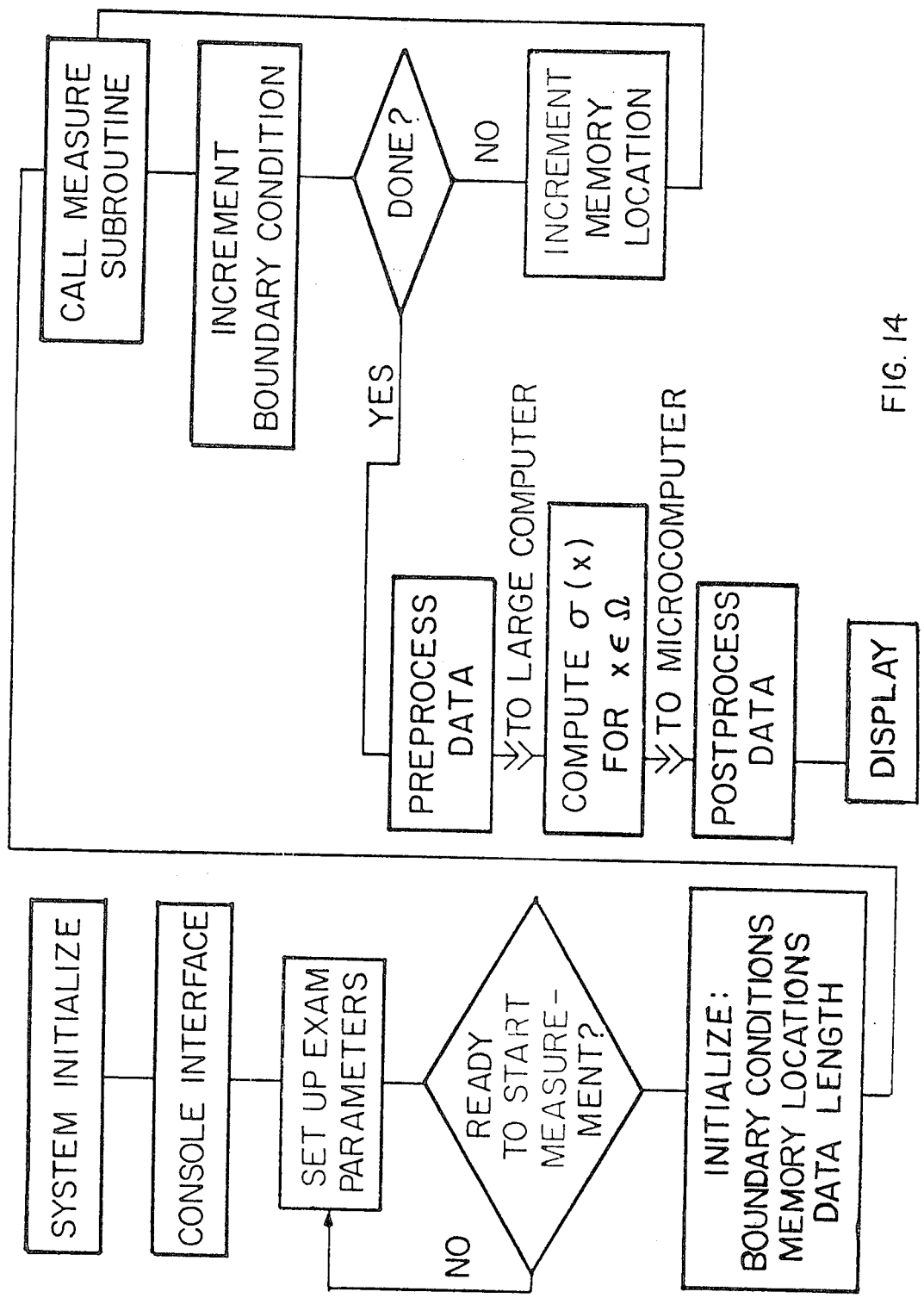

The overall operation of the electronic processor 44 (FIG. 5) will be summarized with reference to flow charts appearing as FIGS. 14 and 15. FIG. 14 shows an overall program while FIG. 15 is a flow chart for a single boundary condition.

Referring now to FIG. 14, it is appreciated that there are four phases of operation which can be summarized as follows:
1. Setup—where the operator and system communicate with each other through the system console.
2. Measurement—where the boundary conditions are established and data is acquired and stored.
3. Computation—which is carried out partially by the microcomputer and mostly by the large computer.
4. Display—which may be a tabulation of numberical data or a CRT or hard copy.

In the setup phase the operator selects the desired boundary conditions and then presses a return key to initiate the measurement process. The measurement phase includes an initialization step, to reset the boundary condition counter and to specify the starting address of microcomputer memory and amount of the data in bytes to be measured. After initialization the measurement routine of FIG. 15 is carried out.

Referring now to FIG. 14, it is seen that the boundary condition counter is incremented and if all the boundary conditions have not been implemented, the measurement cycle is repeated.

Once all data has been entered, the computation phase begins. Some preprocessing can be done by the microcomputer. For example, the values of $q_m(x)$ can be computed and averaged (if more than 1 cycle/electrode is measured).

The large computer calculates $\sigma(x)$ from the known and measured quantities $p_m(x)$ and $q_m(x)$ and sends back the results to the microcomputer. In simplest form, the displays phase comprises a sequence of 2-dimensional data corresponding to parallel cuts through the domain $\Omega$, printed in tabular form.

The measurement subroutine of FIG. 15 is operative to control the entire electronic processing procedure and comprises three phases:
(1) Boundary condition generation
(2) Data acquisition
(3) Data transfer First, the selected boundary condition is passed onto the electronic processor 44. Next, a START command is issued to the boundary condition modules. The modules then begin to establish a boundary condition. Since the READY lines of all modules are connected in a wired-OR configuration (FIG. 9), the last module to finish establishing the boundary conditions sets the READY status. After the READY status is detected, an optional delay may be implemented in order to allow transients to die down.

Data acquisition is accomplished in a similar manner. First, a START command is issued to each data acquisition module. The modules begin to measure data. Since the READY lines of all data acquisition modules are connected in a wired-OR configuration, the last module to finish establishes the READY status. When READY status is achieved, the data transfer phase is entered. As mentioned before, the RAM address space is contiguous across all data modules. Therefore, the program reads in the data sequentially via the data input port, until all of the data has been read into the microcomputer memory.

Data from the microcomputer is transferred to the large computer by standard techniques. The large computer implements the procedures discussed separately, generating a three-dimensional solution for (x). Since the large computer may be in a remote central location, the solution (x) is transferred back to the microcomputer.

It is appreciated that the simplest useful form of presentation of the data is a tabulation of results. However, color, gray scale and three dimensional display techniques may also be used.

It will be appreciated by persons skilled in the art that the invention is not limited to what has been particularly shown and described above. Rather the scope of the present invention is defined only by the claims which follow:

We claim:
1. Apparatus for use in electric tomography comprising:

a coupling medium for receiving an object to be examined;

a plurality of electrodes disposed in communication with said coupling medium and arranged in a three dimensional array generally surrounding the object to be examined;

multiplexing and measuring means for applying electric voltages at selected first pluralities of electrodes and simultaneously measuring electric currents including non-straight line currents at corresponding selected second pluralities of electrodes in a desired sequence;

computation means coupled to said multiplexing means for initially estimating the values of the electrical properties at a multiplicity of locations in the object to be examined, said locations being arranged in a three dimensional imaginary grid defined in the object to be examined and subsequently correcting the initially estimated values of the electrical properties at each of said multiplicity of locations by solving an inverse Laplace equation using the applied electric voltages and electrical current measurements provided by said multiplexing and measuring means by an iterative process; and means for providing a visible tomographic representation of the values of the electrical properties at each of said multiplicity of locations as determined by said computation means.

2. Apparatus according to claim 1 and wherein said first pluralities of electrodes are arranged to provide non-parallel currents flowing through the object to be examined in response to application of electric voltages thereto by said multiplexing means.

3. Apparatus according to claim 2 and wherein said plurality of electrodes is arranged to substantially surround the object to be examined.

4. Apparatus according to claim 3 and wherein said plurality of electrodes are arranged to lie along surfaces which include surfaces which are mutually perpendicular.

5. Apparatus according to claim 2 and wherein said plurality of electrodes are arranged to lie along surfaces which include surfaces which are mutually perpendicular.

6. Apparatus according to claim 1 and wherein said plurality of electrodes is arranged to substantially surround the object to be examined.

7. Apparatus according to claim 6 and wherein said plurality of electrodes are arranged to lie along surfaces which include surfaces which are mutually perpendicular.

8. Apparatus according to claim 1 and wherein said plurality of electrodes are arranged to lie along surfaces which include surfaces which are mutually perpendicular.

9. A method for carrying out electric tomography comprising the steps of:

providing a coupling medium for receiving an object to be examined;

arranging a plurality of electrodes in electrical contact with said coupling medium in a three dimensional array generally surrounding said object to be examined;

selectably energizing various combinations of said electrodes in a desired sequence and measuring the currents including non-straight line currents between various combinations of said electrodes as the result of such energization;

computing the values of the electrical properties of the interior of the object from the measured currents; and providing a visible tomographic representation of the computed values of the electrical properties of the interior of the object.

10. A method according to claim 9 and wherein said selectably energizing step comprises energizing combinations of electrodes to produce non parallel currents flowing through said object.

* * * * *